United States Patent

Sunnen et al.

[11] 3,955,571
[45] May 11, 1976

[54] RECHARGEABLE APPLICATOR FOR DISPENSING SUBSTANCES

[75] Inventors: Robert M. Sunnen; Jerome J. Siegel, both of St. Louis; Harold T. Rutter, Kirkwood, all of Mo.

[73] Assignee: The Emko Company, St. Louis, Mo.

[22] Filed: Apr. 3, 1974

[21] Appl. No.: 457,415

[52] U.S. Cl. .................. 128/235; 128/225
[51] Int. Cl.² ........................ A61M 37/00
[58] Field of Search .......... 222/402.21, 402.22, 222/402.23, 402.2, 386; 128/218 G, 218 M, 218 D, 220, 225, 237, 238, 251, 260, 261, 235

[56] References Cited
UNITED STATES PATENTS

| 2,763,406 | 9/1956 | Countryman | 222/402.21 |
| 3,154,076 | 11/1964 | O'Donnell | 128/225 X |
| 3,154,224 | 11/1964 | Wakeman | 222/402.21 X |
| 3,161,196 | 12/1964 | Berkow | 222/402.21 X |
| 3,357,427 | 12/1967 | Wittke et al. | 128/225 X |
| 3,612,359 | 10/1971 | Sundholm | 222/386 |
| 3,677,246 | 7/1972 | Stein | 128/218 D |
| 3,682,175 | 8/1972 | Halter | 128/235 |

Primary Examiner—Robert B. Reeves
Assistant Examiner—Larry H. Martin
Attorney, Agent, or Firm—Charles B. Haverstock

[57] ABSTRACT

A rechargeable applicator for dispensing substances especially substances in a foam or foam-like condition including dispensing them into body cavities or elsewhere, the applicator includes a pressurized container having one end which is normally closed by a valve and filled with a substance under pressure for dispensing therefrom, and cooperatively associated with the container is an expandable chamber into which some of the contents of the container can be expelled in a foam or foam-like condition when the container is withdrawn but not separated from the chamber, the container thereafter serving as a plunger for expelling the contents of the chamber into a body cavity or elsewhere where the substance is to be used.

6 Claims, 7 Drawing Figures

U.S. Patent  May 11, 1976  3,955,571
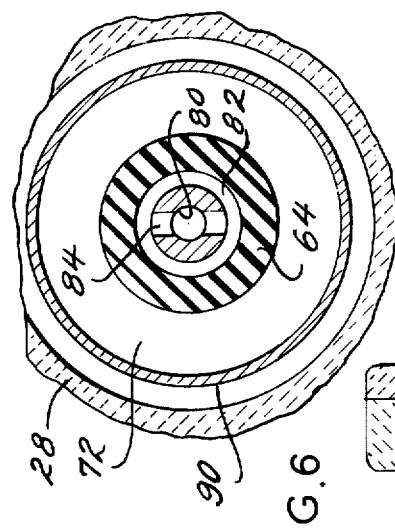
FIG. 6
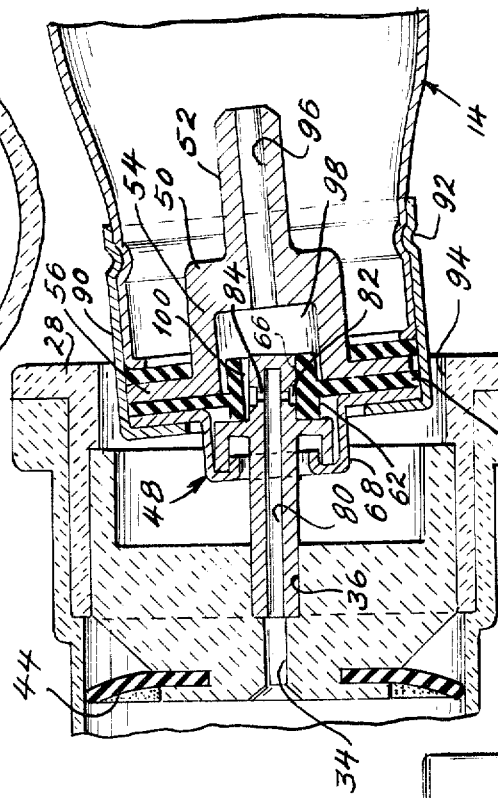
FIG. 5
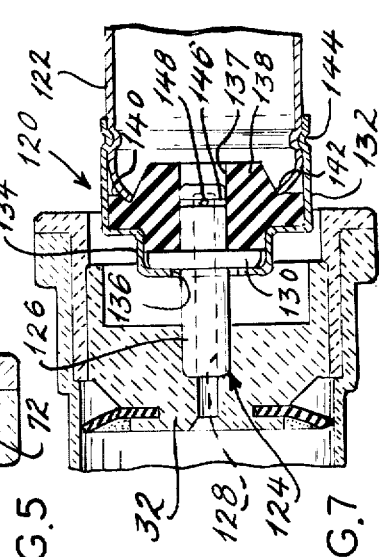
FIG. 7
FIG. 1
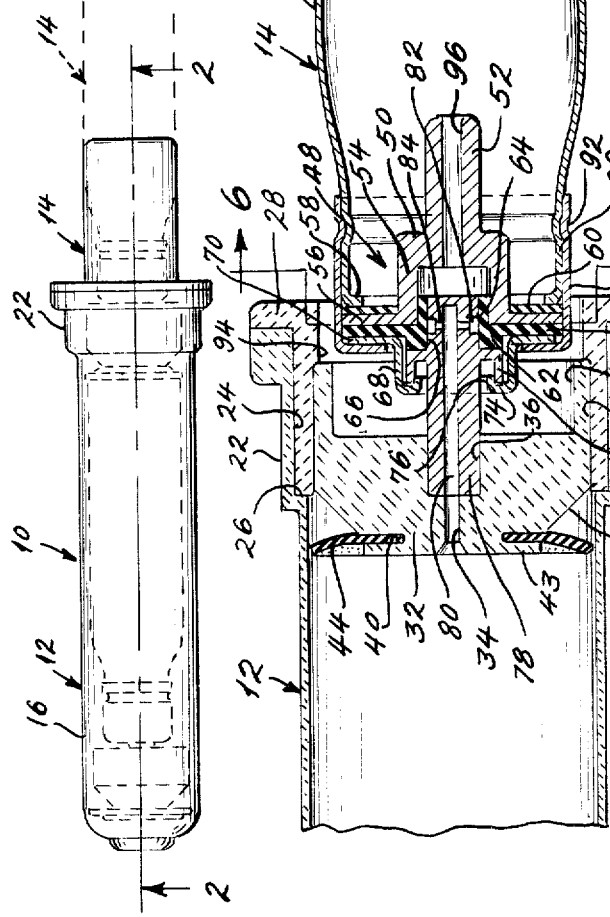
FIG. 4
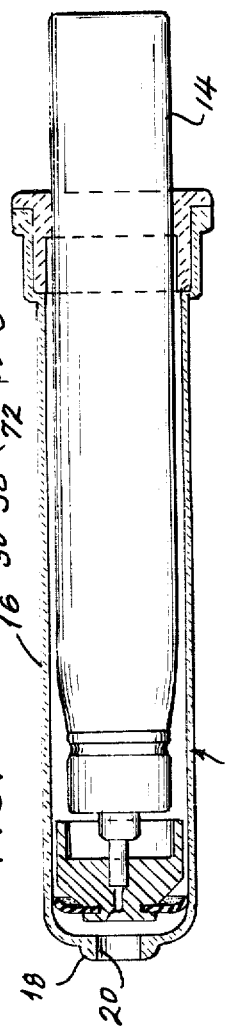
FIG. 2
FIG. 3

3,955,571

RECHARGEABLE APPLICATOR FOR DISPENSING SUBSTANCES

Applicators of various types and constructions have been devised and used heretofore including some which are used for dispensing substances in a foam or foam-like condition and including medicinal and other substances which prior to being dispensed are stored under pressure. Some of the known applicators have been designed and constructed particularly for dispensing substances into body cavities. Typical of the known prior art applicators used for dispensing substances in a foam or foam-like condition into body cavities are those applicators disclosed in Sunnen U.S. Letters Pat. Nos. 3,220,413, dated Nov. 30, 1965, 3,540,448, dated Nov. 17, 1970 and 3,656,482, dated Apr. 18, 1972. The devices disclosed in these patents include means constructed to cooperate with valve means on an aerosol type container to receive therefrom a charge of the substance to be dispensed. In each of the patented constructions, after the applicator has been filled from the aerosol container, the applicator is separated from the aerosol container and thereafter the applicator is used to dispense the charge it has received. Some of the known devices have also been constructed for dispensing individual accurately measured dosages received from precharged containers or cartridges that have valve means which cooperate with means on the applicator device. One of the disadvantages of prior art devices is that they require separate aerosol container and separate applicator means, or they require that the user maintain a supply of precharged single dosage containers which have the further disadvantage of having limited shelf-life because they tend to lose their charge, and their contents have a tendency to settle and separate. The known devices for the most part also are relatively messy and wasteful to use, they are inconvenient because they are cumbersome, complicated and require the keeping track of and cleaning several different components, they are not convenient to carry and they are unreliable and relatively expensive to construct.

The present construction overcomes these and other disadvantages and shortcomings of the known devices, and teaches the construction and operation of a novel, one-piece charged container and applicator which can be constructed as an assembly, the parts of which cooperate to accurately measure each dosage, and thereafter, cooperate in dispensing or applying of same. Furthermore, the subject construction can be made to be relatively more compact than any known construction for the same or similar purpose, and it is extremely easy and accurate to use. It can also be made to be small enough to be easily carried in a purse or pocket, and it can be made so as to minimize the waste and mess normally associated with such devices.

It is therefore a principal object of the present invention to provide an improved combination charged container and applicator for dispensing substances and particularly substances in a foam or foam-like condition.

Another object is to provide accurate means for measuring dosages of a substance to be dispense in a foam or foam-like condition.

Another object is to combine in an assembly a charged aerosol container and an applicator in such a way that the charged container becomes the source of supply as well as the means by which the product is dispensed from the applicator.

Another object is to teach the construction and operation of a relatively inexpensive applicator which can be easily and accurately operated even by persons having relatively little skill and training.

Another object is to minimize waste and clean-up procedures in the dispensing of substances and particularly substances which are dispensed into body cavities.

Another object is to overcome shelf-life problems associated with substances dispensed in measured dosages.

Another object is to minimize the size and compactness of an assembly formed by a charged container and an applicator.

Another object is to provide improved means to control the dispensing of an aerosol product from an aerosol container.

Another object is to provide more accurate means for observing and controlling the dispensing of the contents of an aerosol container into an applicator.

These and other objects and advantages of the present invention will become apparent after considering the following detailed specification which discloses and describes preferred embodiments thereof in conjunction with the accompanying drawings; wherein:

FIG. 1 is a side elevational view showing an assembly formed by an aerosol container and an applicator constructed according to the present invention, said aerosol container being shown in solid outline in one position and in dotted outline in a different operating position;

FIG. 2 is a somewhat enlarged side elevational view partly in section showing the subject container and associated applicator in assembled and inoperative condition with the container positioned inside of the applicator;

FIG. 3 is a side elevational view partly in section showing the container in an extended position withdrawn from the applicator portion of the assembly;

FIG. 4 is a further enlarged fragmentary cross-sectional view showing more of the details of the valve and valve operator means of the container portions of the device of FIGS. 1–3;

FIG. 5 is a still further enlarged fragmentary cross-sectional view similar to FIG. 4 but showing the container valve means in an actuated open condition;

FIG. 6 is a cross-sectional view taken on line 6—6 of FIG. 4; and,

FIG. 7 is an enlarged cross-sectional view showing another form of valve means for use in the subject device.

Referring to the drawings more particularly by reference numbers, number 10 identifies an assembly which includes an applicator portion 12 and a container portion 14. The container portion 14 may be an aerosol type container. The container 14 is attached to the applicator portion 12 and the portions operate in conjunction with each other.

The applicator portion 12 has a tubular wall 16 which may be constructed of a plastic or plastic-like material including especially a transparent or translucent plastic material. One end of the applicator tube 16 is partially closed by an end wall portion 18 that has an opening 20 formed therein. The opening 20 is the dispensing opening for the subject device when the device is being used to dispense a substance such as into a body cavity or the like. The opposite end of the tubular housing 12 has an annular flange portion 22 which is shown slightly larger in diameter than the tubular portion 16, and the flange 22 has an inside annular surface 24 which terminates at shoulder 26. The annular surface 24 frictionally receives another annular member 28 which is shown having its outer surface engaged therewith. The member 28 has an inner surface 30 which slidably receives yet another member 32 which is a plunger member for the applicator 12. The plunger member 32 has a centrally located orifice or passage 34 which communicates at one end with the inside of the applicator portion 12, and at its opposite end with larger diameter stepped bores 36 and 38. The plunger 32 also has an outside annular groove 40 formed between a tapered portion 42 thereof and an annular end portion 43, and an annular relatively stiff but resilient gasket 44 of rubber or reinforced rubber or plastic is positioned in the groove 40 and extends outwardly therefrom for engagement with the inner surface of the cylindrical portion 16 of the applicator 12. In the construction as shown, the outer diameter of the gasket 44 is made to be slightly larger in diameter than the inside diameter of the applicator 12 so that it is slightly curved in a generally forward direction to slidably and sealably make engagement with the inner surface of the wall portion 16.

The aerosol container portion 14 of the subject device includes a container 46 shown as being an elongated container having an outside diameter that is approximately the same as the inside diameter of the applicator portion 12. The container 46 is closed at one end and has valve means 48 attached to the opposite end thereof as clearly shown in FIGS. 4 and 5. The valve means 48 are formed by an assembly of members including a stepped flanged tubular member 50 which includes a tubular portion 52 which extends into the container 14 and may have a dip tube attached thereto, a connected larger diameter portion 54, and an outwardly extending annular flange portion 56. The annular flange 56 is positioned adjacent to the curved open end 58 of the container 14 and is sealed thereto by means of an annular flexible gasket 60 which is positioned therebetween. The opposite side of the flange 56 from the gasket 60 is positioned adjacent to a flexible valve member or gasket 62 which has a portion 64 that extends into the tubular portion 54 of the member 50. The gasket 62 has a central orifice or passage 66 which extends therethrough as shown in FIGS. 4 and 5, and a flanged metal member 68 is positioned having one portion 70 positioned adjacent to the outwardly extending portion 72 of the member 62, and a second tubular portion which terminates in inwardly curved flanges 74 and 76, the flange 76 extending back toward the insider of the container 14.

A tubular valve operator member 78 is positioned extending through the flange 76 between an outwardly extending and an inwardly extending portion which is sealably engaged with the inner surface 66 of the resilient valve member 62. The tubular member 78 has a counter bore 80 which extends into it from the outer free end thereof and terminates at a location near the opposite or inner end. Adjacent to the inner closed end of the member 78 and formed on the outer surface thereof is an annular outside groove 82 which communicates with the counter bore 80 through one or more radially extending passages 84. In the normal closed condition of the valve means 48, the outside groove 82 is sealably engaged with the surface 66 of the resilient member 62, and this engagement prevents communication between the inside of the container 14 and the outlet passage formed by the counter bore 80.

The tubular valve member 78 has an outwardly extending annular flange portion 86 which is L-shaped in cross-section and has its free edge extending into an annular cavity defined by the flanges 74 and 76 on the member 68. This holds the members together in a way that permits relative movement therebetween. The valve members including the resilient members 60 and 62 and the non-resilient members including the flange 56 on the member 50 and the member 68 are attached to the neck portion 88 of the container 14 by means of a flanged closure member 90. When the valve members are assembled in the closure member 90 in the positions as shown in FIGS. 4 and 5, the closure member 90 is pressed onto the neck end of the container and under pressure the closure member 90 and the neck portion 88 are grooved or crimped as at 92 to hold them together.

With the container and its associated valve means constructed and assembled as indicated above, the container is attached to the applicator portion 12 by pressing the free end of the tubular portions 78 into the bore 36 in the member 32. The press fit between the members 78 and 32 should unite the members sufficiently so that they will not easily come apart, a condition necessary and desirable for best operation. With the parts assembled and connected as described, it is possible to move the container 14 while attached to the applicator 12 between the positions shown in FIGS. 2 and 3. The position shown in FIG. 2 is a position in which a substantial portion of the aerosol container is positioned inside of the applicator 12, and the position shown in FIG. 3 is the position wherein the aerosol container 14 is in its most extended position relative to the applicator 12. In the extended positions of the container 14 sufficient clearance is provided between the flanged container closure member 90 and the adjacent annular surface 94 of the member 28 to enable the container 14 to be tilted relative to the applicator to a position such as that shown in FIG. 5 wherein the valve means are opened. This position is achieved while retaining all of the members in their assembled condition. When the valve means 48 are opened, the pressurized contents of the container 14 can pass through the passage 96 in the tubular portion 52 of the member 50 and into the chamber 98 also in the member 50. From there the contents can move through a space 100 which is now formed by and between the closed end portion of the member 78 and the adjacent resilient member 64. The substance that passes into the space 100 can also enter the annular outside groove 82 and the radial passages 84 to enter the counter bore 80. From there, the exiting substance passes into the bore 34 and escapes into the applicator 12 ahead of the gasket 44. If the applicator 12 is made of a transparent or translucent material the user can watch the substance as it is being emitted from the container 14 into the applicator and can easily tell when to stop emitting substance from the container when the applicator is filled. When the desired filled condition is reached, the operator can reclose the valve 48 by restoring the container 14 to its non-tilted position. The same condition can also be determined by noticing when the substance being emitted into the applicator starts to come out through the outlet orifice 20. After the applicator portion 12 has been filled to the desired amount from the aerosol container 14 in the manner described, it can be dispensed therefrom where needed by holding the applicator portion in one hand while pushing on the container 14 in the directon to move it into the applicator to the position shown in FIG. 2. As this is being done the gasket 44 will move along and scrape the inner surface of the applicator thereby minimizing any loss or waste. This can be done even while the applicator is inserted into a body cavity. Thereafter, the device can be cleaned if desired by dipping the open end of the applicator portion 12 into a cleaning substance such as into warm water and then by moving the aerosol container back and forth can produce a pumping action which draws in and discharges the water with a cleaning and rinsing action.

It is contemplated to make all of the parts of the applicator portion of the subject device of a plastic or plastic-like material and it is also contemplated to make all of the parts which frictionally fit together relatively difficult to take apart although this possibility is contemplated also. This means that the annular member 28 should be made to be relatively difficult to remove from the applicator 12 and the same is true of the connection between the members 78 and 32.

In FIG. 7 is shown a modified form of valve means 120 for use on the aerosol container 122. The modified valve means 120 include a valve operator member 124 which has an elongated portion 126 with a counter bore 128 that extends from the free end thereof to near to the opposite end which is the end that is positioned inside of the aerosol container 122. The member 124 also has an outwardly extending annular flange 130 which is located at an intermediate position and is positioned inside of a flanged metal container closure member 132. The diameter of the flange 130 is made to be slightly smaller than the inside diameter of the wall portion 134 of the closure 132. The closure 132 also has an opening 136 which is somewhat larger in diameter than the diameter of the tube portion 126.

The inner end portion of the tubular portion 126 extends into a passage 137 formed in a resilient or rubber-like member 138. The member 138 has a portion which is shaped to conform generally to the internal shape of the closure member 132 when positioned as shown, and the member 138 also has a surface which faces the inside of the container 122 which is defined by a shoulder 140 against which the open end edge 142 of the container 122 is pressed to sealably close the container. When assembled as described, the closure member 132 is crimped to the container 122 as at crimping 144 to hold the members together in assembled condition. The tube portion 126 which extends into the rubber-like member 138 has an annular outside groove 146 which communicates with one or more radial openings or orifices 148.

The free end of the operator member 124 is positioned extending into a member similar to the member 32 in the construction described above, and the modified valve construction 120 operates similarly to the constructions described above except that when the container 122 is tilted relative to the applicator portion of the device, the annular flange 130 tilts inside of the closure 132 and in so doing tilts and moves the inner portion of the member 124 relative to the passage 137 in the resilient member 138 thereby forming a space between these members so that the contents of the aerosol container can escape through the communicating passages 148 and 128 by way of the annular groove 146. The corresponding parts of the applicator portion of the modified construction shown in FIG. 7 are similar to those described above and are similarly numbered in the drawings.

Thus there has been shown and described novel assemblies which combine an applicator and a container such as an aerosol container that fulfill all of the objects and advantages sought therefor. It will be apparent, however, to those skilled in the art, that many changes, modifications, variations, and other uses and applications of the subject construction are possible. All such changes, modifications, variations and other uses and applications which do not depart from the spirit and scope of the invention are deemed to be covered by the invention which is limited only by the claims which follow.

What is claimed:

1. An assembly combining a dosage applicator and a charged container, the applicator including a tubular member partially closed at one end to define a discharge outlet, said tubular member including a substantially continuous side wall extending from the discharge outlet to adjacent the opposite end, said tubular member having an uninterrupted inner surface, a piston member slideably and sealably positioned in the applicator portion and movable therein between the opposite ends, said container including a housing adapted to be moved into and out of the applicator, valve means attached to one end of the container, said valve means including a valve stem portion which projects endwardly from the container and through which the contents of the container are expelled when the valve means are in their open condition, said stem portion being movable on the container between an inoperative position in which the valve means are closed and an operative position angularly related to the inoperative position in which the valve means are open, means connecting the projecting valve stem portion to the piston member for movement in concert therewith in the applicator, said piston member having passage means therethrough that communicate with the passage means in the valve stem portion, the container and the applicator including the piston member being relatively angularly movable only when the piston member is positioned in the applicator adjacent to the end thereof opposite from the partially closed end in which position the container is substantially withdrawn from the applicator whereby the stem portion of the valve means can be moved to the open position to permit discharge of some of the contents of the container into the applicator, said container and the attached piston member being thereafter movable in the applicator toward the partially closed end thereof to force the contents of the applicator out through the discharge outlet.

2. The assembly defined in claim 1 wherein said piston member includes a flexible gasket which extends outwardly therefrom on the side thereof nearest to the partially closed end of the tubular member to make slideable and sealable engagement with the inside of the applicator.

3. The assembly defined in claim 1 wherein the valve stem portion is frictionally engaged with the piston member.

4. The assembly defined in claim 1 wherein the applicator, the piston member and the container including the container valve means are separable from each other under pressure for cleaning and maintenance purposes.

5. The assembly defined in claim 1 wherein the valve means include a resilient tubular member having a passage extending therethrough, said valve stem portion having a first portion which extends from the free end of the container and an opposite second portion which is positioned extending into the resilient tubular member in sealable engagement therewith, said passage through said stem portion including a counterbore extending into the stem portion from the free end thereof and extending to adjacent the opposite end which is inside the container, and radial passage means through the stem portion adjacent the inner end, said radial passage means being normally closed by engagement with the resilient member when the valve stem portion is in the inoperative position.

6. The combination in a single unit of a tubular dosage applicator and an aerosol container having a size and length to be moved into and out of the tubular applicator, the tubular applicator including a tubular member partially closed at one end and an uninterrupted cylindrical inner surface extending from said one end to adjacent the opposite end thereof, a piston member slideably positioned in said tubular member including a reslient gasket extending outwardly from one side thereof for slideable and sealable engagement with the uninterrupted inner surface of the applicator, said piston member having a passage therethrough axially aligned with the cylindrical surface of the applicator, said aerosol container having opposite ends one of which is closed and the other of which has normally closed valve means thereon, said valve means including a resilient closure member with a passage therethrough and an operator member positioned in said passage, said operator member having a bore extending therein from the free end thereof and a transverse opening extending from said bore to adjacent the passage in the resilient member so that the valve means can be moved from a normally closed position to an open position when the operator member is angularly tilted relative to the axis of the aerosol container, means for attaching the free end of the valve operator member to the piston member in communication with the passage therethrough, means to limit withdrawal of the aerosol container from the applicator to a position in which the container is in a substantially extended position therefrom and in which the aerosol container can be tilted relative to the operator member, the piston member, and the applicator to dispense material contained in the aerosol container into the applicator portion, the material dispensed into the applicator portion being dispensed through the partially open end of the tubular applicator when the aerosol container including the valve operator member and the piston member attached thereto are moved telescopically into the applicator portion.

* * * * *